(12) United States Patent
Hashimoto et al.

(10) Patent No.: US 8,211,688 B2
(45) Date of Patent: Jul. 3, 2012

(54) **PROCESS FOR PRODUCING L-GLUTAMINE USING *ESCHERICHIA COLI* WITH DEFICIENT GLNB AND GLNE FUNCTION**

(75) Inventors: Shin-ichi Hashimoto, Hofu (JP); Kazuhiko Tabata, Machida (JP)

(73) Assignee: Kyowa Hakko Bio Co., Ltd., Toyko (JP)

( * ) Notice: Subject to any disclaimer, the term of this patent is extended or adjusted under 35 U.S.C. 154(b) by 200 days.

(21) Appl. No.: 11/630,396

(22) PCT Filed: Jun. 24, 2005

(86) PCT No.: PCT/JP2005/011637
§ 371 (c)(1),
(2), (4) Date: Dec. 22, 2006

(87) PCT Pub. No.: WO2006/001380
PCT Pub. Date: Jan. 5, 2006

(65) Prior Publication Data
US 2008/0038786 A1    Feb. 14, 2008

(30) Foreign Application Priority Data
Jun. 25, 2004    (JP) .................................. 2004-189012

(51) Int. Cl.
C12P 13/14    (2006.01)
C12N 1/20    (2006.01)
(52) U.S. Cl. ..................................... 435/252.1; 435/110
(58) Field of Classification Search .................. 435/110, 435/252.8
See application file for complete search history.

(56) References Cited

U.S. PATENT DOCUMENTS

| | | | |
|---|---|---|---|
| 5,939,295 A | 8/1999 | Dunkak et al. | |
| 2003/0003550 A1* | 1/2003 | Nakamura et al. | 435/110 |
| 2003/0148474 A1* | 8/2003 | Gusyatiner et al. | 435/110 |
| 2005/0287626 A1 | 12/2005 | Hashimoto et al. | |

FOREIGN PATENT DOCUMENTS

| | | |
|---|---|---|
| EP | 1 424 398 | 6/2004 |
| EP | 1 460 128 | 9/2004 |
| JP | 2002-300887 A | 10/2002 |
| JP | 2003-164297 A | 6/2003 |
| JP | 2004-283167 | 10/2004 |

OTHER PUBLICATIONS

Bowie et al (Science, 1990, 247:1306-1310).*
International Search Report of PCT/JP2005/011637, mailed Sep. 6, 2005.
Jakoby et al., "Nitrogen regulation in *Corynebacterium glutamicum*: isolation of genes involved and biochemical characterization of corresponding proteins," FEMS Microbiol. Lett., Apr. 15, 1999, vol. 173, No. 2, pp. 303-310.
Bueno et al., Role of glnB and glnD gene products in regulation of the glnALG operon of *Escherichia coli*, J. Bacteriol., 1985, vol. 164, No. 2, pp. 816-822.
Merrick et al., "Nitrogen control in bacteria," Microbiol. Rev., 1995, 12, vol. 59, No. 4, pp. 604-622.
Reitzer "Ammonia Assimilation and the Biosynthesis of Glutamine, Glutamate, Aspartate, Asparagine, L-Alanine, and D-Alanine", *E. coli* and *Salmonella*, Second Edition (1996), pp. 391-407.
Noden et al "Glutamine synthetases of *Corynebacterium glutamicum*: transcriptional control and regulation of activity", FEMS Microbiology Letters 201 (2001) 91-98.
Haruo et al, Patent Abstracts of Japan "Production of L-Arginine through Fermentation Process", JP 57-005693, Jan. 12, 1982.
Kuniki et al "Method for Preparing Amino Acid by Fermentation Method", JP 2001-086998, Apr. 3, 2001.
Masahiro et al "Method for Producing Nucleotide by Fermentation Method", JP 2002-355087, Dec. 10, 2002.
"Metabolic Pathways" (www.Sigma-aldrich.com/pathways) Sigma-Aldrich, 22d Ed. (2003).
Lehninger, Biochemistry, 2d ed. (1975) 693-727 (The Biosynthesis of Amino Acids and Some Derivatives; Metabolisms of Inorganic Nitrogen).
Lehninger, Biochemistry, 2d ed. (1975) 729-47 ("The Biosynthesis of Nucleotides").
Griffiths et al., "Genetic Code", NCBI (2000) http://www.ncbi.nlm.nih.gov/books/NBK21950/#A1854.

* cited by examiner

*Primary Examiner* — Ram R Shukla
*Assistant Examiner* — Nina Archie
(74) *Attorney, Agent, or Firm* — Fitzpatrick, Cella, Harper & Scinto

(57) ABSTRACT

The present invention provides a microorganism belonging to the genus *Escherichia* in which the activities of glutamine-synthetase adenylyltransferase (GlnE protein) and PII regulatory protein for glutamine synthetase are reduced or lost and which has the ability to form and accumulate L-glutamine or a substance biosynthesized utilizing nitrogen supplied by L-glutamine, and a process for producing L-glutamine or the substance biosynthesized utilizing nitrogen supplied by L-glutamine using the microorganism.

12 Claims, No Drawings

PROCESS FOR PRODUCING L-GLUTAMINE USING *ESCHERICHIA COLI* WITH DEFICIENT GLNB AND GLNE FUNCTION

This application is the US national phase of international application PCT/JP2005/011637, filed 24 Jun. 2005, which designated the U.S. and claims priority of JP 2004-189012, filed 25 Jun. 2004, the entire contents of each of which are hereby incorporated by reference.

TECHNICAL FIELD

The present invention relates to a microorganism belonging to the genus *Escherichia* which has the ability to form and accumulate L-glutamine or a substance biosynthesized utilizing nitrogen supplied by L-glutamine, and a process for producing L-glutamine or the substance using the microorganism.

BACKGROUND ART

In microorganisms belonging to the genus *Escherichia* and the like, L-glutamine serves not only as a substrate for protein synthesis, but also as a nitrogen-supplying substrate in the biosynthesis of purine and pyrimidine nucleic acids and amino acids such as L-arginine, L-histidine, L-tryptophan and L-asparagine.

On the other hand, L-glutamine biosynthesis is catalyzed by glutamine synthetase (GS) encoded by the glnA gene and it is known that GS activity is subject to very strict and complicated regulation. That is, GS is negatively controlled by adenylylation. Such adenylylation and deadenylylation are catalyzed by glutamine-synthetase adenylyltransferase (hereinafter referred to as GlnE protein) encoded by the glnE gene, and the direction of catalysis is determined by PII regulatory protein for glutamine synthetase (hereinafter referred to as GlnB protein) encoded by the glnB gene. When the GlnB protein is uridylylated, it promotes deadenylylation of GS by the GlnE protein, and on the contrary, when the GlnB protein is not uridylylated, it promotes adenylylation of GS by the GlnE protein. The uridylylation and deuridylylation of the GlnB protein are determined by a protein encoded by the glnD gene. As L-glutamine promotes deuridylylation, GS is adenylylated to cause a lowering of GS activity, leading to regulation suppressing L-glutamine synthesis. On the other hand, 2-oxoglutaric acid promotes uridylylation of the GlnB protein, whereby L-glutamine synthesis is promoted according to the scheme opposite to the above (non-patent publication Nos. 1 and 2).

Attempts have been made to produce L-glutamine by fermentation by deregulating the above-described complicated mechanism. In patent publication No. 1, it is described that *Escherichia coli* which forms and accumulates L-glutamine was obtained by modifying GS so that its adenylylation site shall not be adenylylated and by enhancement of the expression of the glnA gene, but the L-glutamine production by the microorganism is only 1.3 g/l.

Further, the following microorganisms are known: glutamine-producing strains such as *Corynebacterium plutamicum* having glnE gene deletion (patent publication No. 2) and *Corynebacterium plutamicum* in which the glnA gene is modified and the expression of the gdh gene is enhanced (patent publication No. 2); L-arginine-producing strains such as *Escherichia coli* into which the ghA gene was introduced (patent publication No. 3); L-tryptophan-producing strains such as *Escherichia coli* into which the tryptophan operon, aroG gene and serA gene were introduced (patent publication No. 4); L-histidine-producing strains such as *Escherichia coli* conferred aminoquinoline resistance (patent publication No. 5); and nucleic acid-producing strains such as 5'-inosinic acid-producing *Escherichia coli* in which the purA, deoD, purR, add, gsk, edd, xapA, ushA and aph genes are deleted and the expression of the desensitized purF gene is enhanced (patent publication No. 6) and 5'-guanylic acid-producing *Escherichia coli* in which the purA, deoD, purR, add, gsk, edd, xapA, ushA and aph genes are deleted and the expression of the desensitized purF gene and the guaAB gene is enhanced (patent publication No. 6). However, there has been no report on a microorganism belonging to the genus *Escherichia* in which the activities of the GlnE protein and the GlnB protein are reduced or lost and which has the ability to form and accumulate L-glutamine or a substance biosynthesized utilizing nitrogen supplied by L-glutamine, and a process for producing L-glutamine or the substance using the microorganism.

Non-patent publication No. 1:
  *E. coli* and *Salmonella*, Second Edition (1996)
Non-patent publication No. 2:
  FEMS Microb. Lett., 201, 91-98 (2001)
Patent publication No. 1:
  Japanese Published Unexamined Patent Application No. 164297/03
Patent publication No. 2:
  Japanese Published Unexamined Patent Application No. 300887/02
Patent publication No. 3:
  Japanese Published Unexamined Patent Application No. 5693/82
Patent publication No. 4:
  U.S. Pat. No. 5,939,295
Patent publication No. 5:
  Japanese Published. Unexamined Patent Application No. 86998/01
Patent publication No. 6:
  Japanese Published Unexamined Patent Application No. 355087/02

DISCLOSURE OF THE INVENTION

Problems to be Solved by the Invention

An object of the present invention is to provide a microorganism belonging to the genus *Escherichia* which has the ability to form and accumulate L-glutamine or a substance biosynthesized utilizing nitrogen supplied by L-glutamine, and a process for producing L-glutamine or the substance using the microorganism.

Means for Solving the Problems

The present invention relates to the following (1) to (10).

(1) A microorganism belonging to the genus *Escherichia* in which the activities of glutamine-synthetase adenylyltransferase (hereinafter referred to as GlnE protein) and PII regulatory protein for glutamine synthetase (hereinafter referred to as GlnB protein) are reduced or lost and which has the ability to form and accumulate L-glutamine or a substance biosynthesized utilizing nitrogen supplied by L-glutamine.

(2) The microorganism according to the above (1), wherein the microorganism belonging to the genus *Escherichia* is a microorganism in which a nucleotide is deleted, substituted or added in the nucleotide sequence of the gene encoding the wild-type GlnE protein (hereinafter referred to as glnE gene) and in that of the gene encoding the wild-type GlnB protein (hereinafter referred to as glnB gene).

(3) The microorganism according to the above (1) or (2), wherein the microorganism belonging to the genus *Escherichia* is *Escherichia coli*.

(4) The microorganism according to any one of the above (1) to (3), wherein the substance biosynthesized utilizing nitrogen supplied by L-glutamine is an amino acid or a nucleic acid.

(5) The microorganism according to the above (4), wherein the amino acid is an amino acid selected from the group consisting of L-arginine, L-tryptophan, L-histidine and L-glutamic acid.

(6) The microorganism according to the above (4), wherein the nucleic acid is a nucleic acid selected from the group consisting of adenosine, inosine, guanosine, xanthosine, cytidine, uridine, thymidine, 5'-adenylic acid, 5'-inosinic acid, 5'-guanylic acid, 5'-cytidylic acid, 5'-xanthylic acid, 5'-uridylic acid and 5'-thymidylic acid.

(7) A process for producing L-glutamine or a substance biosynthesized utilizing nitrogen supplied by L-glutamine, which comprises: culturing the microorganism according to any one of the above (1) to (3) in a medium; allowing L-glutamine or the substance to form and accumulate in the medium; and recovering L-glutamine or the substance from the medium.

(8) The process according to the above (7), wherein the substance biosynthesized utilizing nitrogen supplied by L-glutamine is an amino acid or a nucleic acid.

(9) The process according to the above (8), wherein the amino acid is an amino acid selected from the group consisting of L-arginine, L-tryptophan, L-histidine and L-glutamic acid.

(10) The process according to the above (8), wherein the nucleic acid is a nucleic acid selected from the group consisting of adenosine, inosine, guanosine, xanthosine, cytidine, uridine, thymidine, 5'-adenylic acid, 5'-inosinic acid, 5'-guanylic acid, 5'-cytidylic acid, 5'-xanthylic acid, 5'-uridylic acid and 5'-thymidylic acid.

EFFECT OF THE INVENTION

The present invention provides a microorganism belonging to the genus *Escherichia* which has the ability to form and accumulate L-glutamine or a substance biosynthesized utilizing nitrogen supplied by L-glutamine, and a process for producing L-glutamine or the substance using the microorganism.

BEST MODES FOR CARRYING OUT THE INVENTION

1. Microorganisms Belonging to the Genus *Escherichia* in Which the Activities of the GlnE Protein and the GlnB Protein Are Reduced or Lost and Preparation Thereof The microorganisms belonging to the genus *Escherichia* in which the activities of the GlnE protein and the GlnB protein are reduced or lost can be obtained by the following methods: a method in which glnE and glnB gene deletion mutations present in existing microorganisms belonging to the genus *Escherichia* are accumulated in one microorganism belonging to the genus *Escherichia* by P1 transduction [J. H. Miller, Experiments in Molecular Genetics, Cold Spring Harbor Lab. (1972)]; a method in which mutation treatment such as UV irradiation is performed and then strains in which the activities of the GlnE protein and the GlnB protein are reduced or lost are selected; a method in which nucleotide deletions, substitutions or additions are introduced into the nucleotide sequences of the glnE gene and the glnB gene on the chromosomal DNA of a microorganism belonging to the genus *Escherichia*, and the like. Herein, the glnE gene and the glnB gene respectively consist of a nucleotide sequence wherein a nucleotide sequence containing a region regulating the gene expression such as a promoter sequence is added to the nucleotide sequence encoding the GlnE protein or the GlnB protein.

In the present invention, the microorganisms belonging to the genus *Escherichia* in which the activities of the GlnE protein and the GlnB protein are reduced refer to microorganisms in which the activities of the GlnE protein and the GlnB protein are reduced compared with strains before mutation (parent strains) by introduction of the above mutation, specifically, those in which the protein activities are reduced preferably to 80% or less, preferably 50% or less, more preferably 30% or less, particularly preferably 20% or less, particularly preferably 10% or less, most preferably 5% or less. The activities of the GlnE protein and the GlnB protein can be measured by known methods.

The methods for introducing a deletion, substitution or addition of a nucleotide into a gene on the chromosomal DNA of a microorganism include methods utilizing homologous recombination. An example of a general method utilizing homologous recombination is a method using a plasmid for homologous recombination prepared by ligating a mutant gene having an introduced nucleotide deletion, substitution or addition to a plasmid DNA incapable of autonomous replication in a host cell into which the nucleotide deletion or the like is to be introduced and carrying a drug resistance gene. An example of a preferred method utilizing homologous recombination is a method in which a nucleotide deletion, substitution or addition is introduced by utilizing the homologous recombination system of lambda phage [Proc. Natl. Acad. Sci. USA, 97, 6641-6645 (2000)].

The plasmid for homologous recombination is introduced into a host cell by an ordinary method, followed by selection of a transformant in which the plasmid for homologous recombination has been integrated into the chromosomal DNA by homologous recombination using the drug resistance as a marker. The obtained transformant is cultured using a medium which does not contain the drug for several hours to one day, and then spread on an agar medium containing the drug and on an agar medium without the drug. By selecting a strain which does not grow on the former medium but can grow on the latter medium, the strain in which second homologous recombination occurred on the chromosomal DNA can be obtained. Introduction of a nucleotide deletion, substitution or addition into a desired gene on the chromosomal DNA can be confirmed by determining the nucleotide sequence of a region of the chromosomal DNA containing the gene into which the deletion or the like has been introduced. Further, a nucleotide deletion, substitution or addition can be efficiently introduced into plural genes by utilizing homologous recombination according to a method using a linear DNA.

Specifically, a linear DNA containing a gene into which a nucleotide deletion, substitution or addition is to be introduced is incorporated into a cell to cause homologous recombination between chromosomal DNA and the introduced linear DNA. This method is applicable to microorganisms belonging to the genus *Escherichia* which have the ability to incorporate a linear DNA, preferably those belonging to *Escherichia coli*, more preferably *Escherichia coli* expressing a group of recombinant proteins derived from λ phage (Red recombination system).

An example of *Escherichia coli* expressing λ Red recombination system is *Escherichia coli* JM101. carrying pKD46, which is a plasmid DNA comprising a λ Red recombination system gene (available from *Escherichia coli* Genetic Stock Center, Yale University, U.S.A.).

Examples of the DNAs Useful for Homologous Recombination are as Follows:

(a) linear DNA in which DNAs having homology to DNAs present on the outside of both ends of a region of chromosomal DNA to be subjected to introduction of a nucleotide deletion, substitution or addition are present at both termini of a drug resistance gene;

(b) linear DNA in which DNAs having homology to DNAs present on the outside of both ends of a region of chromosomal DNA to be subjected to introduction of a nucleotide deletion, substitution or addition are ligated to each other;

(c) linear DNA in which DNAs having homology to DNAs present on the outside of both ends of a region of chromosomal DNA to be subjected to introduction of a nucleotide deletion, substitution or addition are present at both termini of DNA consisting of a drug resistance gene and a gene that can be used for negative selection; and (d) linear DNA of the above (a) in which a nucleotide sequence recognized by yeast-derived Flp recombinase [Proc. Natl. Acad. Sci. USA., 82, 5875 (1985)] is additionally present between the drug resistance gene and the DNAs having homology to DNAs present on the outside of both ends of the region of chromosomal DNA.

As the drug resistance gene, any drug resistance genes that impart resistance to a drug to which the host microorganism shows sensitivity can be used. When *Escherichia coli* is used as the host microorganism, examples of the drug resistance genes include kanamycin resistance gene, chloramphenicol resistance gene, gentamicin resistance gene, spectinomycin resistance gene, tetracycline resistance gene and ampicillin resistance gene.

The "gene that can be used for negative selections" refers to a gene that is fatal to a host microorganism under certain culture conditions when the gene is expressed in the host microorganism. Examples of the genes are sacB gene derived from a microorganism belonging to the genus *Bacillus* [Appl. Environ. Microbiol., 59, 1361-1366 (1993)] and rpsL gene derived from a microorganism belonging to the genus *Escherichia* [Genomics, 72, 99-104 (2001)].

The DNAs having homology to the DNAs present on the outside of both ends of a region of chromosomal DNA to be subjected to introduction of a substitution or deletion, which exist at both ends of the above linear DNAs, are located in the same direction as that on the chromosomal DNA, and their length is preferably about 10 bp to 100 bp, more preferably about 20 bp to 50 bp, and further preferably about 30 bp to 40 bp.

The nucleotide sequence recognized by yeast-derived Flp recombinase is not specifically limited so long as it is a nucleotide sequence recognized by the said protein and catalyzing homologous recombination. Preferred examples are DNA having the nucleotide sequence shown in SEQ ID NO: 9, and DNA having a nucleotide sequence wherein one to several nucleotides are deleted, substituted or added in the said DNA and having a nucleotide sequence recognized by yeast-derived Flp recombinase and catalyzing homologous recombination.

The above DNA having homology refers to DNA having such a degree of homology that allows occurrence of homologous recombination between the subject region of chromosomal DNA and the above linear DNA, specifically, 80% or more homology, preferably 90% or more homology, more preferably 95% or more homology, further preferably 100% homology.

The homology among nucleotide sequences can be determined by using algorithm BLAST by Karlin and Altschul [Proc. Natl. Acad. Sci. USA, 90, 5873 (1993)] and FASTA [Methods Enzymol., 183, 63 (1990)]. On the basis of the algorithm BLAST, programs such as BLASTN and BLASTX have been-developed [J. Mol. Biol., 215, 403 (1990)]. When a nucleotide sequence is analyzed by BLASTN on the basis of BLAST, the parameters, for instance, are as follows: score=100 and wordlength=12. When BLAST and Gapped BLAST programs are used, default parameters of each program are used. The specific techniques for these analyses are known (http://www.ncbi.nlm.nih.gov.).

The above linear DNA fragment can be prepared by PCR. The desired linear DNA can also be obtained by constructing DNA containing the above linear DNA on plasmid and then carrying out treatment with restriction enzymes.

More specifically, examples of the methods for introducing a nucleotide deletion, substitution or addition into the chromosomal DNA of a microorganism by utilizing homologous recombination include the following Methods 1 to 4.

Method 1:

A method which comprises introducing the linear DNA of the above (a) or (d) into a host microorganism and selecting a transformant carrying the linear DNA inserted on its chromosomal DNA by homologous recombination using the drug resistance as a marker.

Method 2:

A method which comprises introducing the linear DNA of the above (b) into the transformant obtained according to the above Method 1 and eliminating the drug resistance gene inserted on its chromosomal DNA by Method 1 to substitute or delete a region of the chromosomal DNA of the microorganism.

Method 3:

A Method Which Comprises:

[1] introducing the linear DNA of the above (c) into a host microorganism and selecting a transformant carrying the linear DNA inserted on its chromosomal DNA by homologous recombination using the drug resistance as a marker;

[2] synthesizing DNA by ligating DNAs having homology to the DNAs present on the outside of both ends of a region of chromosomal DNA to be subjected to introduction of a substitution or deletion in the same direction as that on the chromosomal DNA, and introducing the synthesized DNA into the transformant obtained in the above [1]; and

[3] culturing the transformant subjected to the operation of the above [2] under conditions such that the gene that can be used for negative selection is expressed, and selecting a strain capable of growing by the culturing as a strain in which the drug resistance gene and the gene that can be used for negative selection are eliminated from the chromosomal DNA.

Method 4:

A Method Which Comprises:

[1] introducing the linear DNA of the above (d) into a host microorganism and selecting a transformant carrying the linear DNA inserted on its chromosomal DNA by homologous recombination using the drug resistance as a marker; and

[2] introducing a Flp recombinase gene expression plasmid into the transformant obtained in the above [1], and after expression of the gene, obtaining a strain sensitive to the drug used in the above [1].

In the above methods, introduction of the linear DNA into a host microorganism can be carried out by any of the methods for introducing DNA into the microorganism, for example, the method using calcium ion [Proc. Natl. Acad.

Sci. USA, 69, 2110 (1972)], the protoplast method (Japanese Published Unexamined Patent Application No. 248394/88) and electroporation [Nucleic Acids Res., 16, 6127 (1988)].

By using a linear DNA in which an arbitrary gene to be inserted to chromosomal DNA is inserted in the center part of the linear DNA used in Method 2 or Method 3 [2], it is possible to eliminate the drug resistance gene and the like and at the same time to insert an arbitrary gene to the chromosomal DNA.

The above Methods 2 to 4 are methods that leave no foreign genes such as a drug resistance gene and a gene usable for negative selection on the chromosomal DNA of the transformant to be finally obtained. Therefore, it is possible to readily produce a microorganism having nucleotide deletions, substitutions or additions in two or more different regions of the chromosomal DNA by repeating the operations of these methods using the same drug resistance gene and the same gene usable for negative selection.

It is possible to easily confirm that a microorganism in which the activities of the GlnE protein and the GlnB protein are reduced or lost obtained by the above methods has the ability to form and accumulate L-glutamine or a substance biosynthesized utilizing nitrogen supplied by L-glutamine by culturing the microorganism in a medium and then analyzing L-glutamine or the substance formed and accumulated in the medium by a known method such as HPLC analysis or bioassay.

An example of a microorganism belonging to the genus *Escherichia* in which the activities of the GlnE protein and the GlnB protein are lost and which forms and accumulates L-glutamine obtainable by the above methods is *Escherichia coli* JGLBE1 in which the glnE gene and the GlnB gene are deleted.

The above microorganism belonging to the genus *Escherichia* in which the activities of the GlnE protein and the GlnB protein are reduced or lost has not only the ability to form and accumulate L-glutamine but also the ability to form and accumulate a substance biosynthesized utilizing nitrogen supplied by L-glutamine.

Examples of the substances biosynthesized utilizing nitrogen supplied by L-glutamine include amino acids and nucleic acids. Preferred examples of the amino acids include L-arginine, L-histidine, L-tryptophan and L-glutamic acid. Preferred examples of the nucleic acids include adenosine, inosine, guanosine, xanthosine, cytidine, uridine, thymidine, 5'-adenylic acid, 5'-inosinic acid, 5'-guanylic acid, 5'-cytidylic acid, 5'-xanthylic acid, 5'-uridylic acid and 5'-thymidylic acid.

The microorganisms belonging to the genus *Escherichia* in which the activities of the GlnE protein and the GlnB protein are reduced or lost and which have the ability to form and accumulate a substance biosynthesized utilizing nitrogen supplied by L-glutamine include, in addition to *Escherichia coli* JGLBE1, microorganisms obtained by treating the microorganisms obtained by the above methods further by the following methods, alone or in combination:

(a) a method in which at least one of the mechanisms regulating the biosynthesis of the substance is relaxed or canceled;
(b) a method in which the expression of at least one of the enzymes involved in the biosynthesis of the substance is enhanced;
(c) a method in which the copy number of at least one of the enzyme genes involved in the biosynthesis of the substance is increased;
(d) a method in which at least one of the metabolic pathways branching from the biosynthetic pathway of the substance into metabolites other than the substance is weakened or blocked; and
(e) a method in which a cell strain having a higher resistance to an analogue of the substance as compared with a wild-type strain is selected.

When the substance is an amino acid, the methods of the above (a) to (e) are described, for example, in the following literature: (a), Agric. Biol. Chem., 43, 105-111 (1979), J. Bacteriol., 110, 761-763 (1972), Appl. Microbiol. Biotechnol., 39, 318-323 (1993), etc.; (b), Agric. Biol. Chem., 43, 105-111 (1979), J. Bacteriol., 110, 761-763 (1972), etc.; (c), Appl. Microbiol. Biotechnol., 39, 318-323 (1993)., Agric. Biol. Chem., 39, 371-377 (1987), etc.; (d), Appl. Environ. Microbiol., 38, 181-190 (1979), Agric. Biol. Chem., 42, 1773-1778 (1978), etc.; and (e), Agric. Biol. Chem., 36, 1675-1684 (1972), Agric. Biol. Chem., 41, 109-116 (1977), Agric. Biol. Chem., 37, 2013-2023 (1973), Agric. Biol. Chem., 51, 2089-2094 (1987), etc. When the substance is a nucleic acid, the methods of the above (a) to (e) are specifically described in Biotechnology second, completely revised edition, ed. H. J. Rehm, G. Reed, A. Puhler and P. Stadler, vol. 6, "products of primary metabolism" ed. M. Roehr, VCH verlagsgesellschaft mbH, Weinheim (1996), Japanese Published Unexamined Patent Application No. 355087/02, etc.

The microorganisms of the present invention also include microorganisms obtained by subjecting microorganisms belonging to the genus *Escherichia* which are already known to have the ability to produce a substance biosynthesized utilizing nitrogen supplied by L-glutamine to the treatment for causing reduction or loss of the activities of the GlnE protein and the GlnB protein according to the above-described methods.

Known examples of the microorganisms belonging to the genus *Escherichia* which have the ability to produce a substance biosynthesized utilizing nitrogen supplied by L-glutamine include *Escherichia coli* producing L-arginine (Japanese Published Unexamined Patent Application No. 5693/82), *Escherichia coli* producing L-tryptophan (U.S. Pat. No. 5,939,295), *Escherichia coli* producing L-histidine (Japanese Published Unexamined Patent Application No. 86998/01), *Escherichia coli* producing L-glutamic acid (Japanese Published Unexamined Patent Application No. 244970/93), *Escherichia coli* producing 5'-inosinic acid (Japanese Published Unexamined Patent Application No. 355087/02) and *Escherichia coli* producing 5'-guanylic acid (Japanese Published Unexamined Patent Application No. 355087/02).

2. Production Process of the Present Invention

L-Glutamine or a substance biosynthesized utilizing nitrogen supplied by L-glutamine can be produced by culturing in a medium a microorganism belonging to the genus *Escherichia* which can be prepared by the methods described in the above 1, allowing L-glutamine or the substance to form and accumulate in the medium, and recovering L-glutamine or the substance from the medium.

Examples of the substances biosynthesized utilizing nitrogen supplied by L-glutamine include the substances mentioned in the above 1.

The medium used in the production process of the present invention may be any of synthetic media and natural media insofar as it contains nutrients required for the growth of the microorganism of the present invention and the biosynthesis of L-glutamine or a substance biosynthesized utilizing nitrogen supplied by L-glutamine, for example, carbon sources, nitrogen sources, inorganic salts and vitamins.

As the carbon sources, any carbon sources that can be assimilated by the microorganism used can be used. Examples of suitable carbon sources include carbohydrates such as glucose and fructose, alcohols such as ethanol and glycerol, and organic acids such as acetic acid.

Examples of the nitrogen sources include ammonia, ammonium salts such as ammonium sulfate, nitrogen compounds such as amine, and natural nitrogen sources such as peptone and soybean hydrolyzate.

Examples of the inorganic salts include potassium. phosphate, magnesium sulfate, sodium chloride, ferrous sulfate and potassium carbonate.

Examples of the vitamins include biotin and thiamine. Further, if necessary, substances required for the growth of a microorganism of the present invention (e.g., in the case of an amino acid-requiring microorganism, the required amino acid) may be added.

Culturing is preferably carried out under aerobic. conditions, for example, by shaking culture or spinner culture under aeration. The culturing temperature is 20 to 50° C., preferably 20 to 42° C., more preferably 28 to 38° C. The culturing pH is 5 to 9, preferably 6 to 7.5, and the culturing period is 5 hours to 5 days, preferably 16 hours to 3 days.

L-Glutamine or the substance biosynthesized utilizing nitrogen supplied by L-glutamine accumulated in the medium can be recovered by ordinary purification methods. For example, L-glutamine can be recovered by removing cells and solid matters by centrifugation or the like after the culturing and then carrying out ion exchange treatment, concentration or fractional crystallization.

Certain embodiments of the present invention are illustrated in the following examples. These examples are not to be construed as limiting the scope of the present invention.

EXAMPLE 1

Preparation of a Microorganism in Which the glnE Gene and the glnB Gene Are Deleted Deletion of specific genes on *Escherichia coli* chromosomal DNA was carried out according to the method utilizing the homologous recombination system of lambda phage [Proc. Natl. Acad. Sci. USA, 97, 6641-6645 (2000)]. Plasmids pKD46, pKD3 and pCP20 used below were prepared by extraction, according to a known method, from *Escherichia coli* strains carrying them which were obtained from *Escherichia coli* Genetic Stock Center, Yale University, U.S.A.

(1) Cloning of Drug Resistance Gene for Gene Deletion

The nucleotide sequences of the glnE gene and the glnB gene of *Escherichia coli* K12 were already disclosed [Science, 5331, 1453-1474 (1997)]. On the basis of the reported nucleotide sequences, DNAs consisting of the nucleotide sequences shown in SEQ ID NOS: 1 and 2 to be used as primer DNAs for glnE gene deletion and DNAs consisting of the nucleotide sequences shown in SEQ ID NOS: 3 and 4 to be used as primer DNAs for glnB gene deletion were synthesized using a DNA synthesizer (Model 8905, PerSeptive Biosystems, Inc.). The synthesized primer DNAs were designed based on the 36-bp nucleotide sequences that lie upstream and downstream of the respective target genes to be deleted.

PCR was carried out using each set of the above synthetic DNAs as a set of primers and pKD3 DNA as a template. PCR was carried out for 30 cycles of 94° C. for one minute, 55° C. for 2 minutes and 72° C. for 3 minutes, using 40 µl of a reaction mixture comprising 10 ng of the plasmid DNA, 0.5 µmol/l each of the primers, 2.5 units of Pfu DNA polymerase (Stratagene), 4 µl of buffer for Pfu DNA polymerase (10×) (Stratagene) and 200 µmol/l each of deoxyNTPs.

One-tenth of each of the resulting reaction mixtures was subjected to agarose gel electrophoresis to confirm that the desired fragment was amplified. Then, the remaining reaction mixture was mixed with an equal volume of phenol/chloroform (1 vol/1 vol) saturated with TE [10 mmol/l Tris-HCl (pH 8.0), 1 mmol/1 EDTA].

The resulting mixture was centrifuged, and the obtained upper layer was mixed with a two-fold volume of cold ethanol and allowed to stand at −80° C. for 30 minutes, followed by centrifugation to precipitate DNA. Then, the DNA precipitate was dissolved in 20 µl of TE. By this procedure, chloramphenicol resistance gene fragments for deletion of the glnE gene and the glnB gene were obtained.

(2) Preparation of *Escherichia coli* JM101 in Which the glnE Gene on the Chromosomal DNA Is Deleted

*Escherichia coli* JM101 was transformed with pKD46, and *Escherichia coli* JM101 carrying pKD46 (hereinafter referred to as *Escherichia coli* JM101/pKD46) was selected on LB agar medium containing 100 mg/l ampicillin. *Escherichia coli* JM101/pKD46 cultured in the presence of 10 mmol/1 L-arabinose and 50 µg/ml ampicillin was transformed by electroporation using the chloramphenicol resistance gene fragment for glnE gene deletion, and a recombinant strain in which the chloramphenicol resistance gene was inserted into the glnE gene on the chromosomal DNA of JM101 strain and the glnE structural gene was deleted was selected on LB agar medium containing 25 mg/l chloramphenicol.

Replicas of the obtained chloramphenicol-resistant strain were made on LB agar medium containing 25 mg/l chloramphenicol, followed by single colony isolation at 42° C. Then, replicas of the obtained colonies were made on LB agar medium containing 25 mg/l chloramphenicol and LB agar medium containing 100 mg/l ampicillin to select a colony showing chloramphenicol resistance and ampicillin sensitivity. The selected pKD46-eliminated strain was transformed using pCP20, spread on LB agar medium containing 100 mg/l ampicillin, and cultured overnight at 30° C.

Replicas of the ampicillin-resistant strain that grew on the medium were made on drug-free LB agar medium, followed by single colony isolation at 42° C. Then, replicas of the obtained colonies were made on drug-free LB agar medium, LB agar medium containing 25 mg/l chloramphenicol and LB agar medium containing 100 mg/l ampicillin to select colonies showing chloramphenicol sensitivity and ampicillin sensitivity. Chromosomal DNAs were prepared from the respective strains thus obtained according to an ordinary method [Seibutsukogaku Jikkensho (Experiments in Biotechnology), edited by The Society for Biotechnology, Japan, p. 97-98, Baifukan (1992)]. Colony PCR was carried out using primer DNAs consisting of the nucleotide sequences shown in SEQ ID NOS: 5 and 6 which were designed based on an inner nucleotide sequence of the glnE gene.

Colony PCR was carried out for 30 cycles of 94° C. for one minute, 55° C. for 2 minutes and 72° C. for 3 minutes, using 40 µl of a reaction mixture comprising the cells in an amount obtained by contacting a 200-µl pipette tip with the colony, 0.5 µmol/l each of the primers, 2.5 units of Pfu DNA polymerase, 4 µl of buffer for Pfu DNA polymerase (10×) and 200 µmol/l each of deoxyNTPs. Of the strains subjected to PCR, a strain with which no gene amplification was detected was identified as a strain having glnE gene deletion and was designated as *Escherichia coli* JGLE1.

In the same manner as above, *Escherichia coli* JM101/pKD46 was transformed using the chloramphenicol resistance gene fragment for glnB gene deletion to obtain *Escheri-*

*chia coli* in which the glnB gene was deleted, and the obtained strain was designated as *Escherichia coli* JGLB1.

(3) Preparation of *Escherichia coli* JM101 in Which the glnE and glnB Genes on the Chromosomal DNA Are Deleted

*Escherichia coli* JGLE1 obtained in the above (2) was transformed with pKD46, spread on LB agar medium containing 100 mg/l ampicillin, and cultured overnight at 30° C. to obtain *Escherichia coli* JGLE1 carrying pKD46 (hereinafter referred to as *Escherichia coli* JGLE1/pKD46). In the same manner as in the above (2), *Escherichia coli* JGLE1/pKD46 was transformed by electroporation with the chloramphenicol resistance gene fragment for glnB gene deletion to obtain a recombinant strain in which the glnB gene on the chromosomal DNA was deleted. Colony PCR was carried out under the same conditions as in the above (2) using primer DNAs consisting of the nucleotide sequences shown in SEQ ID NOS: 7 and 8 which were designed based on an inner nucleotide sequence of the glnB gene. A strain with which no gene amplification was detected in the above PCR was identified as a strain having glnB gene deletion and was designated as *Escherichia coli* JGLBE1.

EXAMPLE 2

Fermentative Production of L-Glutamine Using the Microorganism in Which the glnE Gene and the glnB Gene Are Deleted (1)

*Escherichia coli* JM101, and *Escherichia coli* JGLB1, *Escherichia coli* JGLE1 and *Escherichia coli* JGLBE1 obtained in Example 1 were respectively inoculated into 8 ml of LB medium [10 g/l Bacto-tryptone (Difco.), 5 g/l yeast extract (Difco) and 5 g/l sodium chloride] in a test tube and cultured at 28° C. for 17 hours. Each of the resulting cultures was inoculated into 8 ml of a production medium [16 g/l dipotassium hydrogenphosphate, 14 g/l potassium dihydrogenphosphate, 5 g/l ammonium sulfate, 1 g/l citric acid (anhydrous), 5 g/l Casamino acid (Difco), 10 g/l glucose, 10 mg/l vitamin $B_1$, 25 mg/l magnesium sulfate heptahydrate and 50 mg/l ferrous sulfate heptahydrate; pH adjusted to 7.2 with 10 mol/l sodium hydroxide; glucose, vitamin $B_1$, magnesium sulfate heptahydrate and ferrous sulfate heptahydrate were added after separate steam sterilization] in a test tube in an amount of 1% and cultured at 30° C. for 24 hours. The resulting culture was centrifuged to obtain a culture supernatant.

The product in the culture supernatant was derivatized by the F-moc method and then analyzed by HPLC. The HPLC analysis was carried out using ODS-HG5 (Nomura Kagaku Co., Ltd.) as a separation column and solution A (6 ml/l acetic acid and 20% (v/v) acetonitrile, pH adjusted to 4.8 with triethylamine) and solution B (6 ml/l acetic acid and 70% (v/v) acetonitrile, pH adjusted to 4.8 with triethylamine) as eluents. The ratio of solution A to solution B was 8:2 during the first 5 minutes of elution and thereafter changed with a linear gradient so that the ratio became 1:1 at 20 minutes after the start of elution. The results of analysis are shown in Table 1.

TABLE 1

|  | L-Glutamine (mg/l) | L-Glutamic acid (mg/l) |
| --- | --- | --- |
| JM101 | 0 | 24 |
| JGLB1 | 0 | 25 |
| JGLE1 | 10 | 53 |
| JGLBE1 | 620 | 29 |

The results shown in Table 1 revealed that *Escherichia coli* JGLBE1 in which the glnE gene and the glnB gene are deleted accumulates a remarkable amount of L-glutamine in the medium compared with *Escherichia coli* JGLB1 or JGLE1 having a single gene deletion in which the glnE gene or the glnB gene is deleted.

EXAMPLE 3

Fermentative Production of L-Glutamine Using the Microorganism in Which the glnE Gene and the glnB Gene Are Deleted (2)

*Escherichia coli* JGLBE1 obtained in Example 1 was inoculated into 50 ml of LB medium in a 300-ml Erlenmeyer flask and cultured at 28° C. for 17 hours.

The resulting culture was inoculated into 950 ml of a production medium for jar fermentation [7 g/l potassium dihydrogenphosphate, 5 g/l ammonium chloride, 1 g/l citric acid (anhydrous), 5 g/l yeast extract (Kyokuto Pharmaceutical Ind. Co., Ltd.), 10 mg/l manganese sulfate heptahydrate, 20 g/l glucose, 10 mg/l vitamin $B_1$, 2 g/l magnesium sulfate heptahydrate and 0.2 g/l ferrous sulfate heptahydrate; pH adjusted to 7.2 with 10 mol/l sodium hydroxide; glucose, vitamin $B_1$, magnesium sulfate heptahydrate and ferrous sulfate heptahydrate were added after separate steam sterilization] in a 2-l jar fermenter in an amount of 1%. Culturing was carried out at 30° C. with stirring (900 rpm) and aeration (compressed air sterilized with a sterilization filter; 1.0 vvm), during which the pH of the medium was maintained at 7.0 with 18% ammonium hydroxide. After the initially added glucose was depleted (after 24 hours), a sterilized 60% glucose solution was supplied at a rate of 10 to 13 ml per hour.

After 50 hours of culturing, the resulting culture was analyzed in the same manner as in Example 2, whereby it was found that 8.0 g/l L-glutamine was accumulated in the culture.

INDUSTRIAL APPLICABILITY

L-Glutamine or a substance biosynthesized utilizing nitrogen supplied by L-glutamine can be efficiently produced by the present invention.

SEQUENCE LISTING FREE TEXT

SEQ ID NO: 1—Description of Artificial Sequence: Synthetic DNA

SEQ ID NO: 2—Description of Artificial Sequence: Synthetic DNA

SEQ ID NO: 3—Description of Artificial Sequence: Synthetic DNA

SEQ ID NO: 4—Description of Artificial Sequence: Synthetic DNA

SEQ ID NO: 5—Description of Artificial Sequence: Synthetic DNA

SEQ ID NO: 6—Description of Artificial Sequence: Synthetic DNA

SEQ ID NO: 7—Description of Artificial Sequence: Synthetic DNA

SEQ ID NO: 8—Description of Artificial Sequence: Synthetic DNA

SEQ ID NO: 9—Description of Artificial Sequence: Synthetic DNA

The invention claimed is:

1. A process for producing a substance, which comprises the steps of: selecting an isolated microorganism in which the activities of glutamine-synthetase adenylyltransferase and PII regulatory protein for glutamine synthetase are lost, and which has the ability to form and accumulate the substance, and wherein the microorganism is an *Escherichia coli* in which at least one nucleotide is deleted, substituted or added in the nucleotide sequence of the gene encoding wild-type glutamine synthetase adenylyltransferase thereby losing such activity, and in which at least one nucleotide is deleted, substituted or added in the nucleotide sequence of the gene encoding wild-type PII regulatory protein for glutamine synthetase thereby losing such activity; culturing the *Escherichia coli* in a medium; allowing the substance to form and accumulate in the medium; and recovering the substance from the medium, wherein said substance is L-glutamine, an amino acid, or a nucleotide biosynthesized using nitrogen supplied from said L-glutamine.

2. The process according to claim 1, wherein the substance is an amino acid, which is selected from the group consisting of L-arginine, L-tryptophan, L-histidine and L-glutamic acid.

3. The process according to claim 1, wherein the substance is a nucleotide, which is selected from the group consisting of adenosine, inosine, guanosine, xanthosine, cytidine, uridine, thymidine, 5'-adenylic acid, 5'-inosinic acid, 5'-guanylic acid, 5'-cytidylic acid, 5'-xanthylic acid, 5'-uridylic acid and 5'-thymidylic acid.

4. The process according to claim 1, wherein the *Escherichia coli* produces at least 620 mg/l L-glutamine, which is either recovered or biosynthesized into said amino acid or said nucleic acid.

5. The process according to claim 2, wherein the *Escherichia coli* produces at least 620 mg/l L-glutamine, which is biosynthesized into said amino acid.

6. The process according to claim 3, wherein the *Escherichia coli* produces at least 620 mg/l L-glutamine, which is biosynthesized into said nucleic acid.

7. The process according to claim 1, wherein said isolated microorganism is *Escherichia coli* JGLBE1.

8. The process according to claim 2, wherein said isolated microorganism is *Escherichia coli* JGLBE1.

9. The process according to claim 3, wherein said isolated microorganism is *Escherichia coli* JGLBE1.

10. The process according to claim 4, wherein said isolated microorganism is *Escherichia coli* JGLBE1.

11. The process according to claim 5, wherein said isolated microorganism is *Escherichia coli* JGLBE1.

12. The process according to claim 6, wherein said isolated microorganism is *Escherichia coli* JGLBE1.

* * * * *

SEQUENCE LISTING

<160> NUMBER OF SEQ ID NOS: 9

<210> SEQ ID NO 1
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
gttgagcggc tgccagagcc tttagccgag gaatcagtgt aggctggagc tgcttc        56

<210> SEQ ID NO 2
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
ctgccagctt gcccgcacca gttcacgctc tgcggtcata tgaatatcct ccttag        56

<210> SEQ ID NO 3
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
ctggacgatg tccgcgaagc actggccgaa gtcggtgtgt aggctggagc tgcttc        56

<210> SEQ ID NO 4
<211> LENGTH: 56
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
tgccgcgtcg tcctcttcac cggtacggat gcgaatcata tgaatatcct ccttag        56

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
agccaaccgc cgcaggccga cgaatgg                                        27

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6

```
ggtcagcgcc atcgcttcct gctcttc                                          27

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
tcccgacacg agctggatgc aaacgat                                          27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
atggaaacat ccggcaaccc ttgacgc                                          27

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
gaagttccta tactttctag agaataggaa cttc                                  34
```